United States Patent [19]

Davis

[11] Patent Number: 5,003,502
[45] Date of Patent: Mar. 26, 1991

[54] DIGITAL FILTER FOR RANDOM VARIABLE

[75] Inventor: James L. Davis, Marlow, Okla.

[73] Assignee: Halliburton Company, Duncan, Okla.

[21] Appl. No.: 262,406

[22] Filed: Oct. 25, 1988

[51] Int. Cl.$^5$ .......................... G06F 15/00; G01T 1/16
[52] U.S. Cl. ..................... 364/572; 166/250;
166/253; 166/292; 250/260
[58] Field of Search ............... 364/550, 555, 572, 554;
377/10, 15, 19, 20, 1; 166/247, 250, 253, 296,
292, 295, 64, 66, 92; 250/256, 259, 260, 253,
482.1, 362, 363.01, 363.04, 366, 369; 73/151,
152, 445, 450

[56] References Cited

U.S. PATENT DOCUMENTS

| | | | |
|---|---|---|---|
| 3,657,532 | 4/1972 | Zimmerman | 250/362 |
| 4,037,459 | 7/1977 | Schlatter | 364/556 X |
| 4,044,602 | 8/1977 | Higgs et al. | 364/556 X |
| 4,395,762 | 7/1983 | Wondergem et al. | 364/554 X |
| 4,480,311 | 10/1984 | Mastain et al. | 377/19 X |
| 4,554,633 | 11/1985 | Glover et al. | 364/572 X |
| 4,562,540 | 12/1985 | Devaney | 250/256 X |
| 4,587,422 | 5/1986 | Bowers | 250/256 X |
| 4,607,694 | 8/1986 | Sah | 73/151 X |
| 4,618,939 | 10/1986 | Davis | 364/555 |
| 4,810,876 | 3/1989 | Wraight et al. | 250/256 |
| 4,820,919 | 4/1989 | Berg et al. | 250/256 X |
| 4,837,705 | 6/1989 | Mussler et al. | 377/10 X |
| 4,857,729 | 8/1989 | Gadeken et al. | 250/256 X |

Primary Examiner—Joseph L. Dixon
Attorney, Agent, or Firm—James R. Duzan; E. Harrison Gilbert, III

[57] ABSTRACT

A digital filter for use with a randomly generated variable, such as in a radioactive densometer, is provided and includes a microprocessor and timing clock for sampling the random variable over a specific time interval. The microprocessor utilizes a weighting factor based upon a first confidence factor and computes the mean value of a first sample of the random variable and compares the number of standard deviations that a subsequent sample is from the mean value of the previous sample and uses a probability related factor to determine if the subsequent sample represents an actual change in density. Further, the microprocessor uses a second confidence factor in determining the weighting factor which counts the number of consecutive times that the subsequent samples are greater than, or less than the mean value and again determines a probability related factor to determine if a change in density is actually occurring. As both the first and second confidence factors increase, so does the weighting factor and the probability that an actual change in fluid density has occurred.

23 Claims, 4 Drawing Sheets

DIGITAL FILTER FOR RANDOM VARIABLE

BACKGROUND OF THE INVENTION

A major portion of the services provided by the oil field service industry relate to cementing operations, including primary cementing, that is, cementing casing into a well bore by pumping cement slurry down a centralized casing and up into the annulus between the well bore and the casing, and squeeze cementing of a particular zone or interval. Additionally, cement slurry is often pumped downhole for water control, fluid loss control, and many other purposes.

Another aspect of the oil field service industry is stimulation services which include, among other operations, fracturing an oil bearing formation by pumping a pressurized fluid into well bore perforations until the oil bearing formation fractures. A proppant laden slurry is then pumped down hole after the fracturing fluid. This fracture is then held open by the proppant, usually sand or bauxite, which remains embedded in the walls of the fracture after the fluid contained within the slurry migrates into the surrounding formation, or, ideally, is flowed back into the well bore out of the formation when pressure is reduced.

In all of the aforementioned situations it would be advantageous to have a quick-response system for determining the density of the cement slurry, or the proppant slurry.

In oil well cementing operations, the density of the cementing slurry is an important factor. The bore hole cementing fluid typically is a slurry of chemical constituents mixed with water and has a certain density. Should the composition of the slurry mixture change during the pumping operation, the density obviously changes and a change in mixture can affect desired results in the cementing operation. For that reason, it is desirable to be able to sense changes in density, i.e. changes in the mixture and to be able to provide a correction to the mixture before a large volume of incorrect mixture is introduced into the system.

Similarly, in fracturing of wells, monitoring of the density of the fracturing fluid, or proppant slurry, is desirable to ensure that there is not too little proppant in the slurry, which can result in fracture closure, or too much proppant, which can result in "sand out", or termination of the operation due to plugging of the pump, lines or well bore with proppant.

It is accordingly, a feature of the present invention to obtain a relatively quick-response time to the change of density in a cementing or fracturing fluid system so that the fluid may be continuously monitored and corrected if necessary to obtain a consistent density for the fluid mixture.

The present invention relates to a method and apparatus for processing randomly generated data to obtain quick response control to changes in the density of a fluid.

The prior art has developed digitally processed data for nuclear densometers, as illustrated by U.S. Pat. No. 3,657,532, issued to Carl W. Zimmerman. As set forth in the '532 patent, digital systems allow the incorporation of extremely reliable, inexpensive and compact integrated circuits and can be used to develop digital pulse counting techniques. However, in this prior art apparatus, there remains a substantially long time response to a change in density in the fluid sample being tested, and as a consequence, a considerable volume of incorrect density fluid may be passed through the system for use before a correction in the density can be detected or made.

Also, U.S. Pat. No. 4,618,939 to Davis and assigned to the assignee of the present invention involves a method and system for sensing the density of a fluid and for providing statistical count signals which are proportional to density. This prior art system only identifies significant changes in density and then responds to these changes only after a substantial period of time.

SUMMARY OF THE INVENTION

A filter for use in a central processing unit (CPU) is provided which can quickly detect actual changes in the state of randomly generated data samples. For example, a radioactive source provides random emissions, some of which are absorbed by the fluid to be measured. The remaining emissions produce counts which are inversely proportional to the density of the fluid. The present invention provides an extremely accurate and quick means of determining whether a change in state (such as density) has actually occurred. The CPU is programmed such that a single deviation of counts with a large number of standard deviations, or multiple deviations of counts with a small or large number of standard deviations in succession having the same sign around the mean will quickly determine when an actual change in state has occurred and update a weighting factor accordingly.

Therefore, in accordance with the previous summary, objects, features and advantages of the present invention will become apparent to one skilled in the art from the subsequent description and the appended claims taken in conjunction with the accompanying drawings.

DESCRIPTION OF THE PREFERRED EMBODIMENTS

Figure 1:
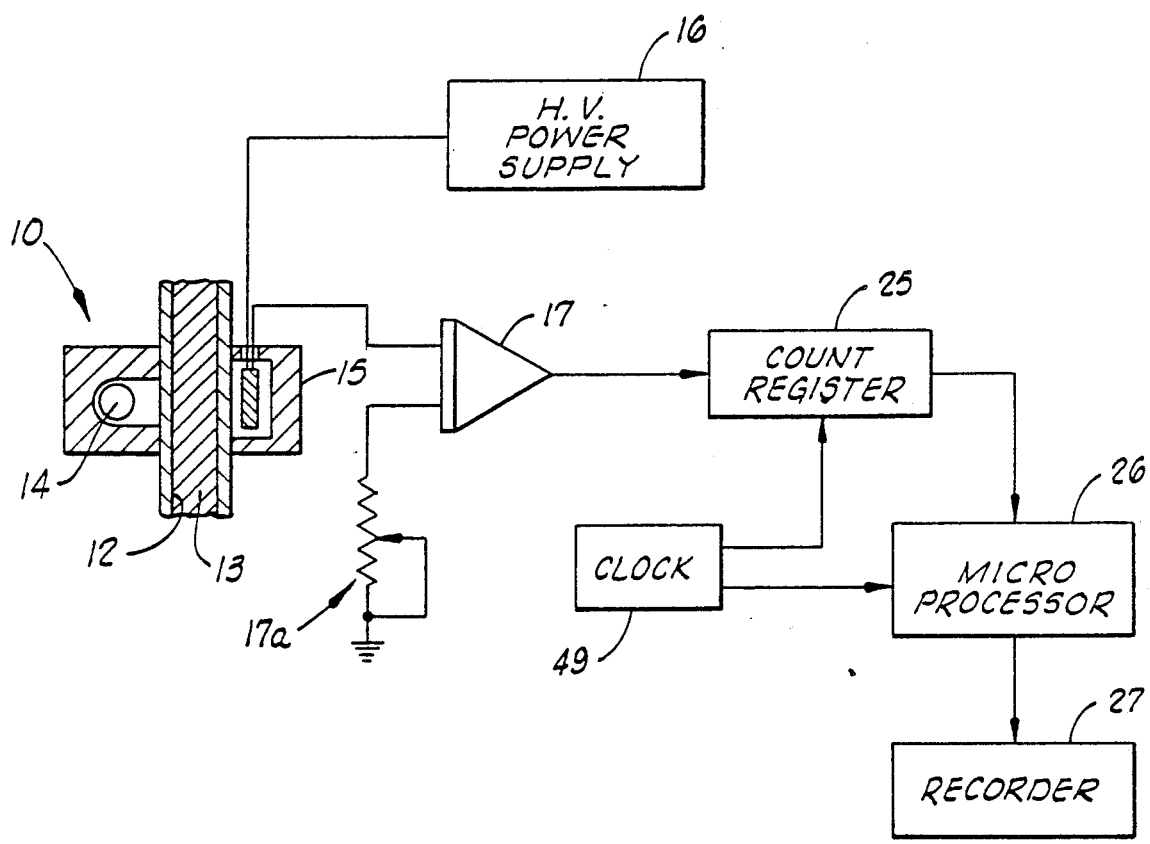
FIG. 1 is a schematic block diagram depicting a radioactive densometer system which can utilize the present invention.

Referring now to FIG. 1, use of the invention in the context of cementing a well bore is described. A housing 10 is mounted on a tubular pipe with a bore 12 through which a well cementing fluid 13 is caused to flow between cementing tanks or trucks (not shown) and a well bore to be cemented (not shown). A source of radiation 14 is located on one side of the bore 12 and, on an opposite side, a radiation detector 15 is located. The radiation provided by the source 14 is a constant intensity over a long period of time (random intensity over a finite period) of gamma ray emissions. The gamma rays are transmitted through the material surrounding the bore 12, the slurry of cement 13 within the bore and to the detector 15. The detector 15 may be, for example, a crystal of sodium or cesium iodide (thallium activated) or other material capable of scintillating under irradiation and may include an electron photo multiplier tube for converting light flashes of the scintillation of the crystal into an electrical pulse. As will be apparent, the only variable with respect to density between the source 14 and detector 15 is the cement slurry 13. A percentage of the gamma rays emitted by the source 14 are absorbed or attenuated by the cement slurry 13 and do not reach the detector 15. Thus the counting rate of the output signal from the photo multiplier tube of the detector 15 is similarly related to the density of cement slurry 13 through which the rays must pass to reach the crystal in the detector 15 and the intensity of the source 14.

The detector 15 is powered by a high voltage power supply 16 and the output signals from the detector 15 are supplied to a comparator circuit 17. The comparator circuit 17 eliminates extraneous noise signals below a selected amplitude level determined by a reference level set by potentioner 17A, and amplifies the output signals which are passed through the circuit. The output of the comparator circuit 17 represents count pulses above the threshold level set by the comparator 17.

The output signals from the comparator 17 are applied to a counter register 25 and the counter register 25 outputs to a computer 26. The computer may be a ZYLOG 16 Bit microprocessor or other suitable CPU. The counter register 25 is keyed by a clock 49 to systematically and regularly process the counts in the register 25 to the computer 26. The computer 26, upon processing of the data, provides an output to a recorder 27.

Before detailing the present invention with respect to processing of data by the computer 26, some background information may be helpful to an understanding of the present invention.

The number of pulses detected by the detector 15 may be shown to be:

$N = Sr_1 \ldots$

Where N is the number of pulses counted during a time period S for randomly generated pulses from a detector and where the counting rate $r_1$ is related to the density of material.

For a fluid material having a given density, the following relationship exists:

$N = KIe^{-at} \ldots$

Where N is the number of pulses detected; K is a constant; $Ie^{-at}$ is the activity of the source at time "t" for a decay factor $a$.

The intensity I may also be stated to be:

$I = I_k{}^{-K/D(u/D)} \ldots$

Where u/D is the mass absorption coefficient of the substance of the bore, $I_k$ is the radiation intensity at the detector with the bore empty, K is a constant dependent upon the width of the bore and D equals the density of the fluid material.

Rewriting the last equation above gives the following:

$$\frac{I}{I_K} = e^{-K/D(u/D)}$$

Figure 2:
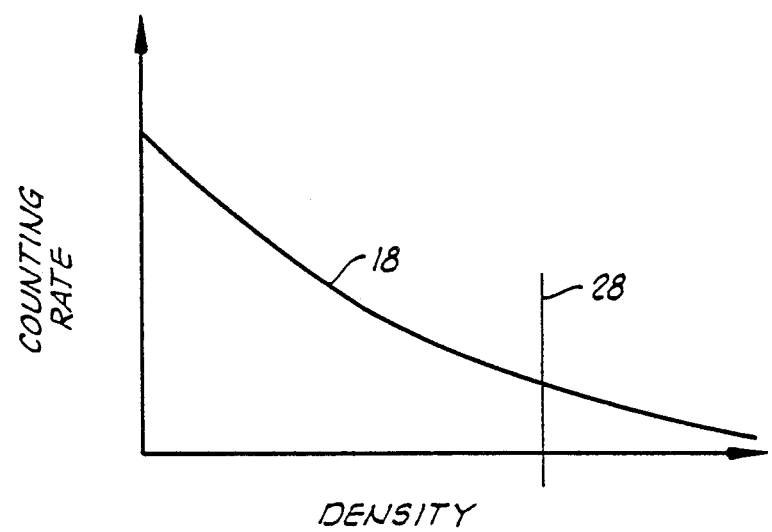
FIG. 2 is a graph illustrating density with respect to count rate.
Figure 2:
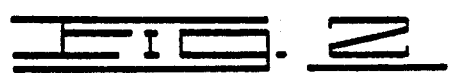

A plot of the counting rate versus density is illustrated by the curve 18 in FIG. 2.

In the operation of the present invention, the detected counts are processed by the comparator 17 and output to the count register 25 and subsequently to the computer 26 on a periodic basis. So long as the density of the slurry is constant, as shown by the vertical line 28 in FIG. 2, the count rate signal is processed using a relatively small weighting factor. However, if there is a large change in density, or if small, or large, changes occur consecutively without a change in sign, a large weighting factor is used to process the count rate signal. The computer 26 samples the accumulated counts signals each tenth of a second, based upon the output of clock 49, and develops a weighting factor. The weighting factor is a function of the change in density of the slurry and if large changes of density occur for a sufficient period of time, or if smaller changes of density occur for a longer period of time consecutively without a change of sign, then the weighting factor is changed to provide a faster indication of the change in density by approximately a factor of ten (or one order of magnitude) than is possible with the filter disclosed by U.S. Pat. No. 4,618,939.

The digital filter of the present invention is described herein with respect to a radioactive densometer, however, it should be noted that the filter is applicable to any system wherein data is randomly generated, such as in many types of well logging.

The present invention greatly reduces response time to an actual change in state of the density by filtering out the unusual random data from the data which indicates that an actual change has occurred and that therefore the weighting factor must be increased to quickly reflect a change in state, such as fluid density.

Figure 3:
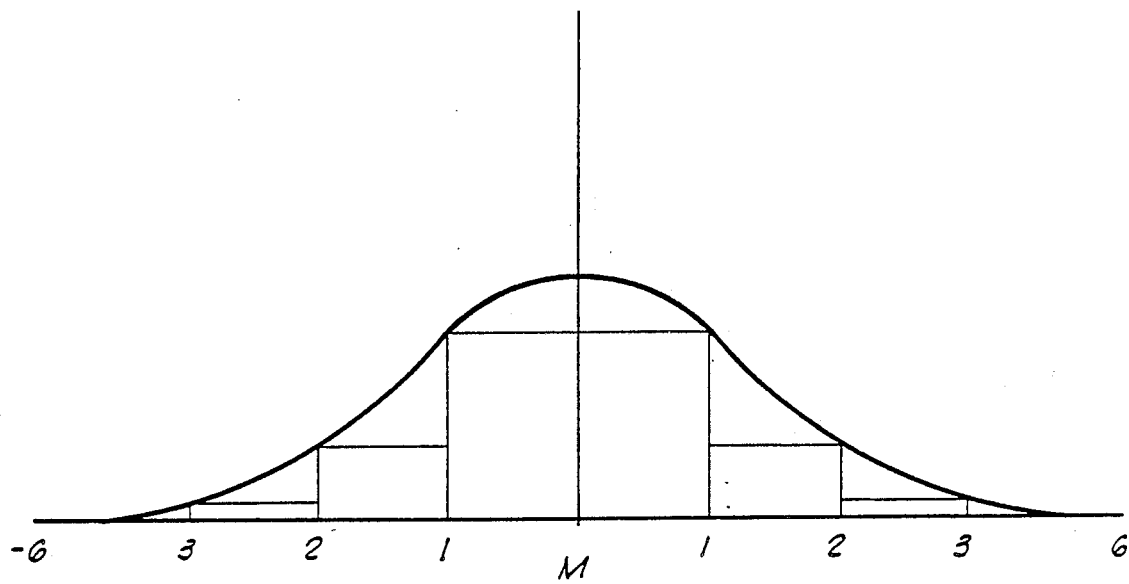
FIG. 3 is a graph representing the normal distribution function of the random counts under steady state conditions.
Figure 3:
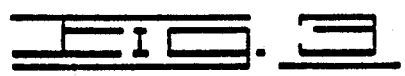

Initially, the filter determines the mean value of the frequency of the counts received, which is shown as M on FIG. 3. The horizontal axis of FIG. 3 represents the number of standard deviations from the mean of the counts. The vertical axis of FIG. 3 represents the probability of occurrence. In other words, FIG. 3 is an illustration of the normal distribution function.

The filter of the present invention uses a combination of two confidence factors in order to obtain a weighting factor.

The first confidence factor uses the probability of random occurrence of statistical deviations relative to the standard deviation. For example, the greater the distance (number of standard deviations) between the mean and the sampled data, the greater the confidence factor. Stated another way, the more standard deviations away from the mean value, the greater the confidence that an actual change in state has occurred. Thus, the weighting factor can be raised as the probability of random occurrences decreases, (i.e. confidence increases).

The second confidence factor uses the fact that the probability of the deviation being either positive or negative is 50 percent over a finite period if no change in state has occurred. That is, randomly generated data is just as likely to be positive (greater than the mean) as negative (less than the mean). Also, for long periods of time, the deviations must be positive, and negative 50 percent of the time. Thus, the more consecutive positive, or negative deviations that occur, the higher the confidence factor that an actual change in state has occurred. Therefore, the weighting factor can be increased since the confidence in the reading has increased.

The mean, as shown on FIG. 3, is changed each time action is taken. The greater the confidence (and thus the greater the weighting factor) the more drastic is the action to be taken. For example, if consecutive data samples are received with three or more positive standard deviations from the mean, then the confidence is high, because the sign of the data has been consecutively positive and three or more standard deviations away from the mean. Thus, fairly drastic action would be taken to change the mean to correspond to the newly received data.

However, if the new data had signs which alternated between positive and negative, and were less than 0.6 standard deviations from the mean, then small action would be taken (i.e. the mean would slowly approach the new data), because the confidence that a change in state has occurred is very low.

As the deviation of the new data approaches zero number of standard deviations from the mean value, there is a low probability that the received data represents an actual change in state of the density. As previously noted, this probability increases as more consecutively positive, or negative data and an increasing number of standard deviations away from the mean is received.

Figure 4A:
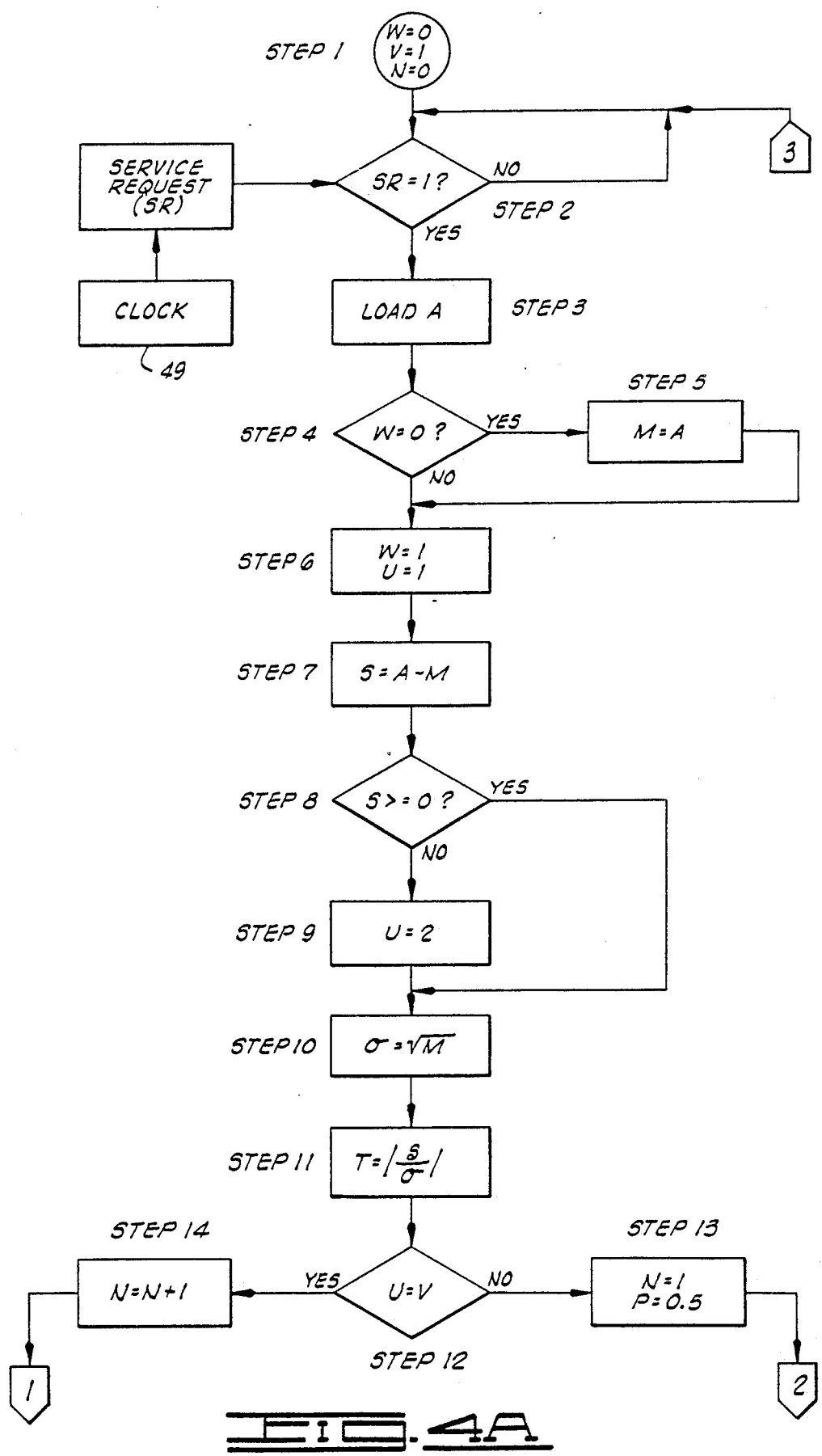
FIGS. 4a and 4b are flow charts for use with a microprocessor, to process the data for obtaining fast response times and indications to changes in state of randomly generated signals.
Figure 4B:
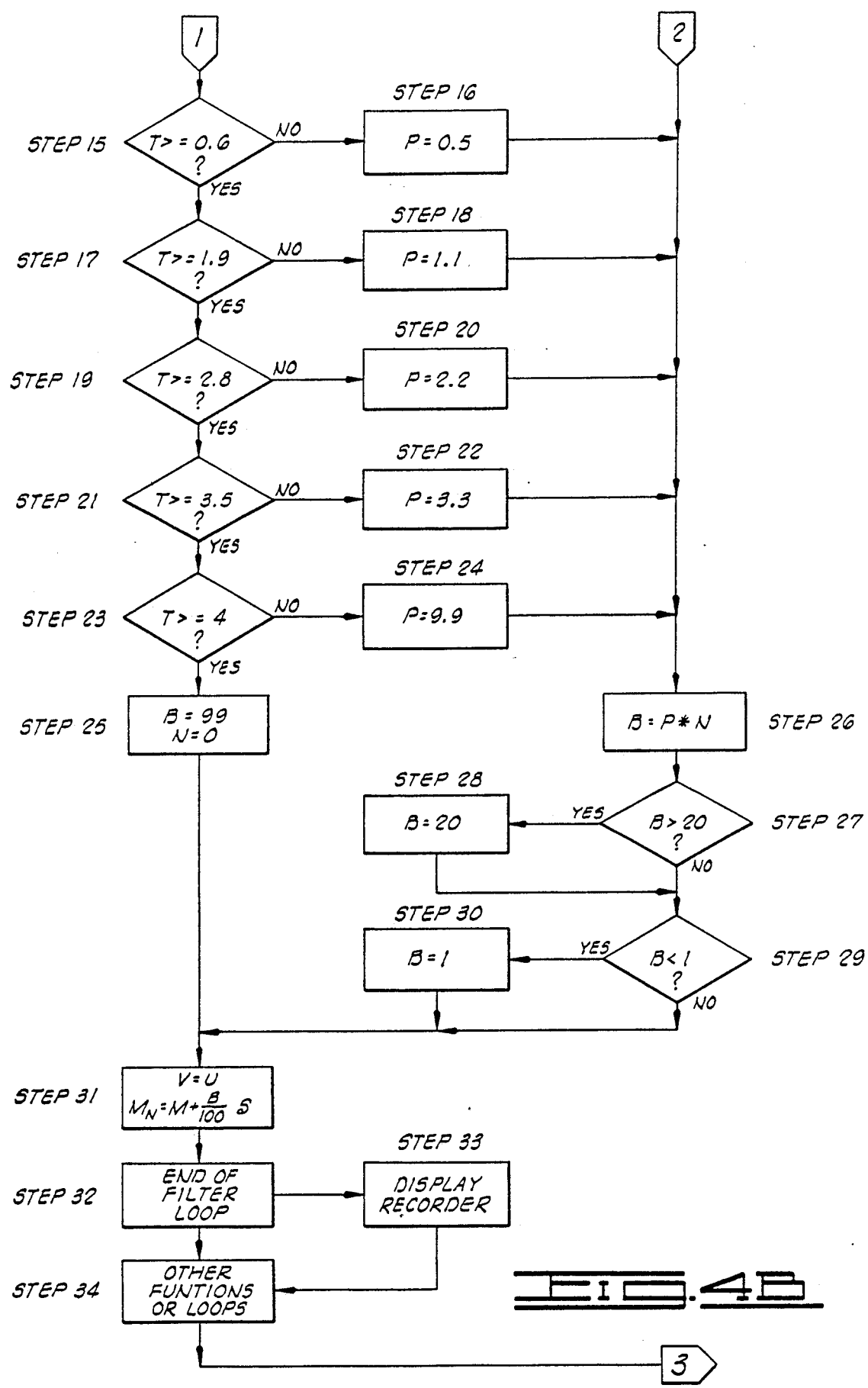

The actual steps which represent filter program to be input to CPU 26 and utilized with the present invention are shown in FIGS. 4a and 4b.

The following variables are used throughout the program:
M mean
SR service request
W determines if first time through filter
A digital value (count)
S difference of current value (count) and the mean
U used to show sign of present S
V used to show sign of previous S
$\alpha$ square root of mean (standard deviation)
T absolute value of the number of standard deviations between the mean and the current value
N consecutive number of times that the sign of S did not change (unless the weighting factor equals 99)
B weighting factor At step 1, W is set to zero, V is set to one and N is set to zero. Step 2 determines if SR is equal to one indicating that clock 49 has initiated a 0.1 second sampling period. If not, then the system returns to the beginning of step 2. If SR is equal to one, then at step 3 the digital value of the radioactive densometer is read.

Step 4 determines if this is the first time through the filter. If so, then at step 5, the counts (A) are designated as the mean (M). If this is not the first time through the filter then W and U are set equal to one (step 6).

Step 7 determines S, i.e. the difference between the mean and counts being processed. Next, at step 8, the filter determines whether S is greater than or equal to zero. If so, the system proceeds to step 10 where the standard deviation of the mean is determined. If, at step 8, S is not greater than or equal to zero, then step 9 sets U, the variable used to show the sign of S, to two.

After the standard deviation is determined, the filter calculates T, the absolute value of the ratio of the difference between the mean and the counts to the standard deviation of the mean (step 11). Next, the present sign of S is compared to the previous sign of S (step 12) and if not equal the system continues to step 13. Step 13 sets the consecutive number of times (N) that the sign did not change to one, and sets a variable P=0.5. P can be used to vary B by the function of P times N and provides more drastic action as the confidence level is increased, i.e. upon consecutive entry of the data into either a positive or negative zone around the mean. After step 13, the filter proceeds to step 26, discussed below.

If at step 12 U is equal to V, then step 14, adds one to the number of consecutive times in which the sign of S did not change.

Steps 15, 17, 19, 21 and 23 determine which band (number of standard deviations the current value is from the mean) the current value is in. Steps 16, 18, 20, 22 and 24 set P to a specific value dependent upon the band and it should be noted that P can only have one value each time a set of data is processed through the loop of the filter. For example, if T is greater than 0.6 (step 15), and if T is less than 1.9 (step 17) then P=1.1 (step 18).

Once a value is assigned to P in one of the steps 13, 16, 18, 20, 22 and 24, the filter proceeds to step 26 where the weighting factor B is determined by multiplying the value of P (determined by one of the steps 12, 15, 17, 19, 21 and 23) by the consecutive number of times the sign of S did not change. Step 27 determines if B is greater than 20. If so, step 28 sets B equal to 20 and the system proceeds to step 29. If, at step 27, B is not greater than 20, then the filter goes directly to step 29 which determines if B is less than one. If B is less than one, then step 30 sets B equal to one and the filter continues to step 31. If B is not less than one at step 29 then the system proceeds directly to step 31.

Steps 27 and 28 are included to slow down the action the filter is taking in order to account for the possibility of an extremely errant random count. Steps 29 and 30 set the minimum action to a value of one in order to ensure that some type of action is always taken. For example, if T is approaching four, at step 23, and the sign has remained constant for a consecutive number of times, such as five, then the filter would take drastic action if step 28 did not slow it down and assign the value 20.

If at step 23, T is greater than four then the filter presumes (at step 25) that, for all practical purposes, a change has most certainly occurred and assigns the value of 99 to B and sets N equal to zero, before proceeding to step 31. By setting N equal to zero the action is slowed for the next time period (second confidence factor is decreased) since the number of times the sign of S did not change for the present set of data will not carry over to the data for the next successive time period.

Step 31 actually determines the type of action the system will take. The previous sign (V) of S is set to be equal to the present sign (U) of S and the new mean (Mn) is determined by the following equation:

$$M_n = M + \frac{B}{100} S$$

Specifically, the new mean is determined by multiplying the weighting factor percent [( B )/100] by the difference between the mean value of the previous sample and the current sample. This product is then added to the current mean value, thereby determining the new mean value.

Therefore, it can be seen how the type of action to be taken by the system depends upon S and B, which are dependent upon the consecutive number of times the sign did not change, and the number of standard deviations the count values are from the mean. When the new mean is determined, then the result is converted to a density representation prior to display on the recorder 27, at step 33.

Finally, after step 31, the filter loop ends at step 32 and step 34 allows any other functions, or loops to be inserted and the system then returns to the beginning of step 2.

While this system is particularly adapted to the measurement of a cement or proppant slurry where extremely good resolution of density measurement is required along with good accuracy and high stability, other adaptations and advantages of the invention will be readily apparent to one skilled in the art to which the invention pertains from a reading of the foregoing. It is accordingly intended that the foregoing description be illustrative only and that the scope of the invention be limited only by the language, with a full range of equivalents, of the appended claims.

What is claimed is:

1. An apparatus utilized by a radiation detection system comprising:
   tubular means for conveying a fluid therethrough;
   a radioactive source means, disposed adjacent said tubular means, for emitting radiation having random intensity over a relatively short period of time and a constant intensity over a relatively long period of time;
   detection means, disposed diametrically opposite said radiation source means and adjacent said tubular means, for detecting said radiation, and for converting said radiation into electrical signals, said radiation being absorbed by said fluid based upon a density thereof and the relationship of fluid density to radiation detected being inversely proportional;
   timing means for sampling said electrical signals for a specific time period; and
   computer means for processing said sampled electrical signals by filtering said electrical signals and by adjusting the present detected density value relative to the previous density value utilizing a weighting factor based upon a first confidence factor and a second confidence factor which indicates that an actual change in the density value has occurred.

2. An apparatus according to claim 1, wherein said computer means determines said first confidence factor based upon a number of standard deviations of the difference between a mean value of electrical signals sampled for previous time periods and a value of electrical signals sampled for a current time period, and said computer means determines said second confidence factor by counting the number of times that said samples of electrical signals are consecutively greater than, or consecutively less than, said mean value.

3. An apparatus according to claim 2 wherein said first confidence factor is directly proportional to the number of standard deviations of the difference between said mean value and said current sample of electrical signals.

4. An apparatus according to claim 3 wherein said second confidence factor is directly proportional to a total number of times that said samples of electrical signals are consecutively greater than, or consecutively less than, said mean value.

5. An apparatus according to claim 4 wherein said weighting factor is directly proportional to both said first confidence factor and said second confidence factor.

6. An apparatus according to claim 5 wherein said weighting factor determines in what proportion said mean value of said previous samples of electrical signals should be adjusted to correspond to said current sample of electrical signals.

7. An apparatus according to claim 6, wherein the adjustment of said mean value is implemented by multiplying said weighting factor, divided by 100, by the difference between said mean value of said previous samples of electrical signals and said current sample of electrical signals, and adding the product to said mean value of said previous samples of electrical signals.

8. A method for radiation detection, comprising the steps of:
   providing a radioactive source which emits radiation having random intensity over a relatively short time period and constant intensity over a relatively long time period;
   providing a detector, linearly aligned with said radioactive source, for detecting said radiation;
   flowing a fluid of a certain density between said detector and said radioactive source;
   detecting said radiation, the amount of said radiation detected being inversely proportional to the density of said fluid;
   converting said radiation into electrical signals;
   sampling said electrical signals over a certain period of time; and
   processing said sampled electrical signals by filtering said electrical signals in accordance with a weighting factor based upon a first confidence factor and a second confidence factor, including:
      setting an initial mean value equal to an initial sample of electrical signals taken during an initial time period;
      calculating a standard deviation of a previously determined mean value;
      determining said first confidence factor by calculating the number of standard deviations of difference between said previously determined mean value and a current sample of electrical signals, said first confidence factor being directly proportional to said number of standard deviations;
   determining said second confidence factor by counting the number of consecutive times the signs of subsequent samples of electrical signals are unchanged with respect to previously determined mean values, said second confidence factor being directly proportional to said number of consecutive times;
   calculating said weighting factor in accordance with said first confidence factor and said second confidence factor; and
   calculating a new mean value based upon said previously determined mean value and the magnitude of said weighting factor, said calculated new mean value being inversely proportional to the density of said fluid.

9. A method according to claim 8 wherein said step of calculating a new mean value is accomplished by utilizing a linear equation.

10. A method according to claim 8 wherein said step of calculating the weighting factor includes the step of reducing the magnitude of said weighting factor in accordance with the likelihood that an errant sample of said electrical signals has been taken.

11. A method according to claim 8 wherein said step of determining said second confidence factor includes adding the number of consecutive times the sign of the difference of said sample of electrical signals did not change for the sample of electrical signals taken during a present time period to the number of consecutive times the sign did not change for any subsequent time periods.

12. An apparatus for processing randomly generated signals used to monitor the density of a fluid, comprising: detection means for detecting said randomly generated signals; sampling means for sampling successive groups of said signals over specific intervals of time; and computer means for filtering said randomly generated signals and for determining whether an actual change in the density of the fluid has occurred, said computer means comparing a mean value of previously sampled signals with a number of standard deviations of a current group of sampled signals and counting the number of times that successive groups of sampled signals remain consecutively greater than, or consecutively less than, said mean value.

13. A system for processing random data, comprising:
means for receiving said random data;
means for sampling said random data over discrete time periods; and
means for processing said sampled random data by filtering said random data and by adjusting a mean value of previous samples of random data relative to a current sample of random data utilizing a weighting factor based upon both a first confidence factor and a second confidence factor which indicate that an actual change in the state of said random data has occurred, wherein:
said first confidence factor is based upon a number of standard deviations between said mean value of said previous samples of random data and a value of said current sample of random data; and
said second confidence factor is determined by counting the number of times that said samples of random data are consecutively greater than, or consecutively less than, said mean value.

14. A system according to claim 13 wherein said first confidence factor is directly proportional to the number of standard deviations of the difference between said mean value of said previous samples of random data and said current sample of random data.

15. A system according to claim 14 wherein said second confidence factor is directly proportional to a total number of times that said samples of random data are consecutively greater than, or consecutively less than, said mean value of said previous samples of random data.

16. A system according to claim 15 wherein said weighting factor is directly proportional to both said first confidence factor and said second confidence factor.

17. A system according to claim 16 wherein said weighting factor determines in what proportion said mean value of said previous samples of random data should be adjusted to correspond to said current sample of random data.

18. A system according to claim 17 wherein said adjustment of said mean value is implemented by converting said weighting factor to a percentage, defining a product by multiplying said percentage by the difference between said mean value and said value of said present sample of random data, and adding said product to said mean value.

19. A method of detecting a change in density of a fluid, comprising the steps of:
(a) determining an initial mean value corresponding to density of the fluid at an initial time; and
(b) determining subsequent mean values, including:
(b1) detecting radiation transmitted through the fluid;
(b2) creating a count in response to the detected radiation;
(b3) subtracting the mean value which has been last determined from said count to define a difference;
(b4) determining whether said difference has a sign which is the same as the sign of a previous difference used in determining said last determined mean value;
(b5) if the sign is different, providing a predetermined weighting factor;
(b6) if the sign is the same, computing a weighting factor in response to the difference and the number of consecutive times the sign has remained the same;
(b7) computing a new subsequent mean value, including adding a percentage, defined by the weighting factor, of said difference to said last determined mean value, wherein a change in said new subsequent mean value from said last determined mean value indicate a change in density of the fluid; and
(b8) repeating said steps (b1) through (b8) to monitor repeatedly for changes in density of the fluid.

20. A method as defined in claim 19, wherein:
said step (b) further includes computing a standard deviation for said last determined mean value and computing a quotient by dividing said difference by said standard deviation; and
said step (b6) includes selecting a value for a variable in response to said quotient and multiplying said selected value by said number of consecutive times the sign has remained the same to define said weighting factor.

21. A method as defined in claim 20, wherein said step (b6) further includes limiting said weighting factor to a predetermined maximum.

22. A method as defined in claim 20, wherein said step (b6) further includes setting said weighting factor to a predetermined maximum in response to said quotient exceeding a predetermined value.

23. A method as defined in claim 19, wherein said steps (b5) and (b6) include defining a minimum positive value for said weighting factor.

* * * * *